US008258283B2

(12) United States Patent
Lee et al.

(10) Patent No.: US 8,258,283 B2
(45) Date of Patent: Sep. 4, 2012

(54) METHOD FOR DETECTION OF HCV AT THE REAL TIME PCR WITH INTERCALATING DYE

(75) Inventors: Dong Hwan Lee, Daejeon (KR); Jin Seok Kang, Daejeon (KR); Jae Sung Lee, Daejeon (KR); Young Suk Park, Daejeon (KR); Dong Hyun Kim, Daejeon (KR)

(73) Assignee: LG Life Sciences Ltd., Seoul (KR)

( * ) Notice: Subject to any disclaimer, the term of this patent is extended or adjusted under 35 U.S.C. 154(b) by 186 days.

(21) Appl. No.: 12/649,239

(22) Filed: Dec. 29, 2009

(65) Prior Publication Data

US 2010/0173284 A1    Jul. 8, 2010

(30) Foreign Application Priority Data

Dec. 29, 2008  (KR) .................. 10-2008-0136112

(51) Int. Cl.
*C12Q 1/68* (2006.01)
*C07H 21/04* (2006.01)
(52) U.S. Cl. .................. 536/24.33; 435/6.1; 435/6.11; 435/6.12; 536/24.3
(58) Field of Classification Search .................. None
See application file for complete search history.

(56) References Cited

U.S. PATENT DOCUMENTS

2006/0046265 A1 * 3/2006 Becker et al. .................. 435/6

FOREIGN PATENT DOCUMENTS

WO    WO 9412670 A2 *  6/1994
WO    WO 2004015131 A2 *  2/2004

OTHER PUBLICATIONS

Martell et al., "High-Throughput Real-Time Reverse Transcription-PCR Quantitation of Hepatitis C Virus RNA," Journal of Clinical Microbiology, 1999, vol. 37, No. 2, pp. 327-332.*
"*Nosema ceranae* BRL01 Nc000962, whole genome shotgun sequence," NCBI Entrez, GenBank Report, Accession No. NW_003313299, Cornman, R.S., et al., Entry Date: Jul. 16, 2010, accessed at http://www.ncbi.nlm.nih.gov/nuccore/300701418?report=GenBank, accessed on Nov. 29, 2010, 1 page.
"*Nosema ceranae* BRL01 Nc000962, whole genome shotgun sequence,"NCBI Entrez, GenBank Report, Accession No. ACOL01000962, Cornman, R.S., et al., Entry Date: Jun. 9, 2009, accessed at http://www.ncbi.nlm.nih.gov/nuccore/239603333, accessed on Jan. 7, 2011, 2 pages.
Cornman, R.S., et al., "Genomic Analyses of the Microsporidian *Nosema ceranae*, an Emergent Pathogen of Honey Bees," *PLoS Pathogens* 5(6): e1000466. doi:10.1371/journal.ppat.1000466, Public Library of Science, United States (Jun. 2009), 14 pages.

* cited by examiner

*Primary Examiner* — Young J Kim
(74) *Attorney, Agent, or Firm* — Sterne, Kessler, Goldstein & Fox P.L.L.C.

(57) ABSTRACT

The present invention relates to a composition for detection of HCV by a single step reaction, comprising a specific primer and probe. In particular, the present invention relates to a composition for detection of HCV by a single step reaction, comprising the primer sequences of SEQ ID NOs:1 and 2; a composition for detection of HCV by a single step reaction, comprising both the primer sequences and a probe of SEQ ID NOs:5 or 9; a method for detecting HCV by a single step reaction, comprising the steps of obtaining a sample from a subject, and amplifying and detecting HCV using the primer and probe; and a kit comprising the primer and probe, in which the HCV detection method is characterized by a single step reaction.

10 Claims, 2 Drawing Sheets

METHOD FOR DETECTION OF HCV AT THE REAL TIME PCR WITH INTERCALATING DYE

CROSS REFERENCE TO RELATED APPLICATIONS

Figure 1:
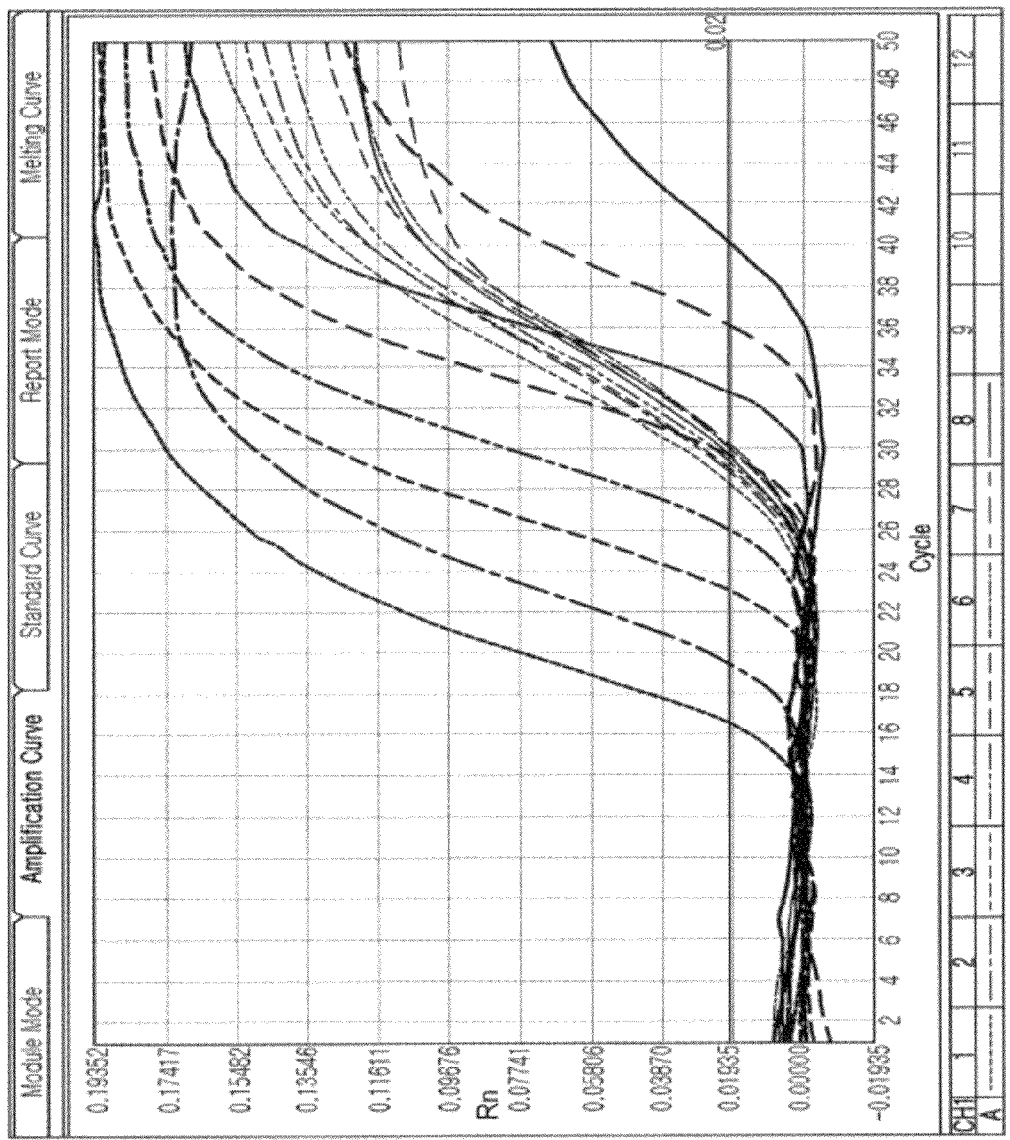

This application claims priority to Korean Patent Application No. 10-2008-0136112, filed Dec. 29, 2008, which is herein incorporated by reference in its entirety.

REFERENCE TO SEQUENCE LISTING SUBMITTED ELECTRONICALLY VIA EFS-WEB

The content of the electronically submitted sequence listing (Name: SEQLIST.txt; Size: 2,208 bytes; and Date of Creation: Dec. 29, 2009) filed herewith the application is incorporated herein by reference in its entirety.

BACKGROUND OF THE INVENTION

1. Field of the Invention

The present invention relates to a composition for detection of HCV by a single step reaction, comprising a specific primer and probe. In particular, the present invention relates to a composition comprising the primer sequences of SEQ ID NOs: 1 and 2 for detection of HCV by a single step reaction, and a method for detecting HCV in blood using a composition comprising the probe of SEQ ID NO:5 or SEQ ID NO:9 for detection of HCV by a single step reaction.

2. Background Art

Hepatitis C virus (HCV), which is a kind of hepatitis virus, is a principal factor in causing serious diseases such as hepatitis including acute hepatitis and chronic hepatitis, which can develop into hepatic cirrhosis and hepatoma. HCV is transmitted via blood transfusion and fluid. It is estimated that about 4 hundred million people over the world are infected with the virus: 0.2-2% of people in the developed countries of Europe, North America and Japan; 2-5% in South America and Asia; over 5% in Africa; and 1.6% (8 hundred thousand) in Korea. See Park et al., *J. Viral Hepat.* 2:195-202 (1995). Unlike hepatitis B virus (HBV), HCV is a virus very threatening to human health in that 50-85% of people infected with hepatitis C virus eventually develop chronic hepatitis. Because HCV is an RNA virus, scientists have not developed any proper remedies and vaccines, much less basic study on HCV yet.

HCV is a positive-strand RNA virus consisting of about 9,500 bases and about 3,000 amino acids. HCV basically consists of an open reading frame (ORF) producing three structural proteins and six non-structural proteins.

Since the HCV level in blood is very low and HCV is an RNA virus, its infection cannot be detected by antigen assays, and thus antibody assays are usually performed. However, the antibody assays are problematic in that the antibodies cannot be detected for a latency period of 6 months after HCV infection. Furthermore, they are not detected in 10% of infected people, which increases the risk of HCV-positive blood transfusion.

On account of the low accuracy of HCV antibody assays, RT-PCR (reverse transcription-polymerase chain reaction) is used for direct detection of HCV RNA. However, there are disadvantages in that the procedures of separately performing reverse transcription and PCR are complicated so as to require skilled persons and much time, and the simultaneous use of two enzymes as in the previous method reduces specificity and sensitivity, and the accuracy of quantitative determination.

Nucleic acid amplification techniques including PCR, which is used to analyze the presence of specific nucleic acids or genes, requires a process of extracting DNA from a sample. The extraction procedures lead to an inevitable loss of DNA. For example, even though a sufficient amount of the target DNA is contained in the sample as a template for amplification, the suitable amount of DNA for amplification could not be recovered due to the loss during the extraction process, leading to a reduction in the amplification efficiency of the template. Therefore, it is hard to sufficiently amplify the target DNA and detect the target DNA in the sample. Consequently, the technique produces a false negative result, and thus it is difficult to ensure accurate results. Even though using the same sample, variations in DNA yields during the extraction process can produce different results, leading to the lack of reproducibility. That is, the DNA amplification technique has problems in that it requires the DNA extraction process to cause the loss of trace target DNA in the sample, whereby the detection sensitivity is reduced. In addition, when amplification inhibitors (e.g., heparin, surfactants, protein denaturants, organic solvents, etc.) are contained in the sample liquid, the amplification efficiency is also reduced lowering the detection sensitivity.

BRIEF SUMMARY OF THE INVENTION

It is an object of the present invention to provide a composition for detection of HCV (Hepatitis C virus) by a single step reaction, comprising the primer sequences of SEQ ID NOs:1 and 2 or further comprising the probe of SEQ ID NOs:5 or 9.

It is another object of the present invention to provide a method for detecting HCV by a single step reaction, comprising the steps of obtaining a sample from a subject; and amplifying and detecting HCV nucleic acid using the primer and probe.

It is still another object of the present invention to provide a kit for detection of HCV, comprising the primer and probe.

EFFECTS OF THE INVENTION

The present invention is directed to methods for detection of HCV by a single step reaction, in which rapid and accurate HCV detection can be performed using a trace amount of target nucleic acid of HCV in a sample, so as to achieve accurate diagnosis of patients with suspected HCV infection, thereby completing the present invention.

As described above, when the detection of HCV infection is performed by the Real-Time PCR according to the present invention, sensitivity and specificity equal to that of the known methods can be obtained. A highly expensive Tth enzyme is used for both reverse transcription and PCR in the known Abbott Real-Time HCV assay, whereas inexpensive enzymes such as MMLV and HS-Taq are used in the present invention to obtain the equivalent or higher diagnosis results. Thus, they are useful for HCV diagnosis.

BRIEF DESCRIPTION OF THE DRAWINGS/FIGURES

FIG. 1 provides the results showing that a positive detection can be made without competitive inhibition of the internal control being specific to GFP for the HCV-specific primer and probe.

Figure 2:
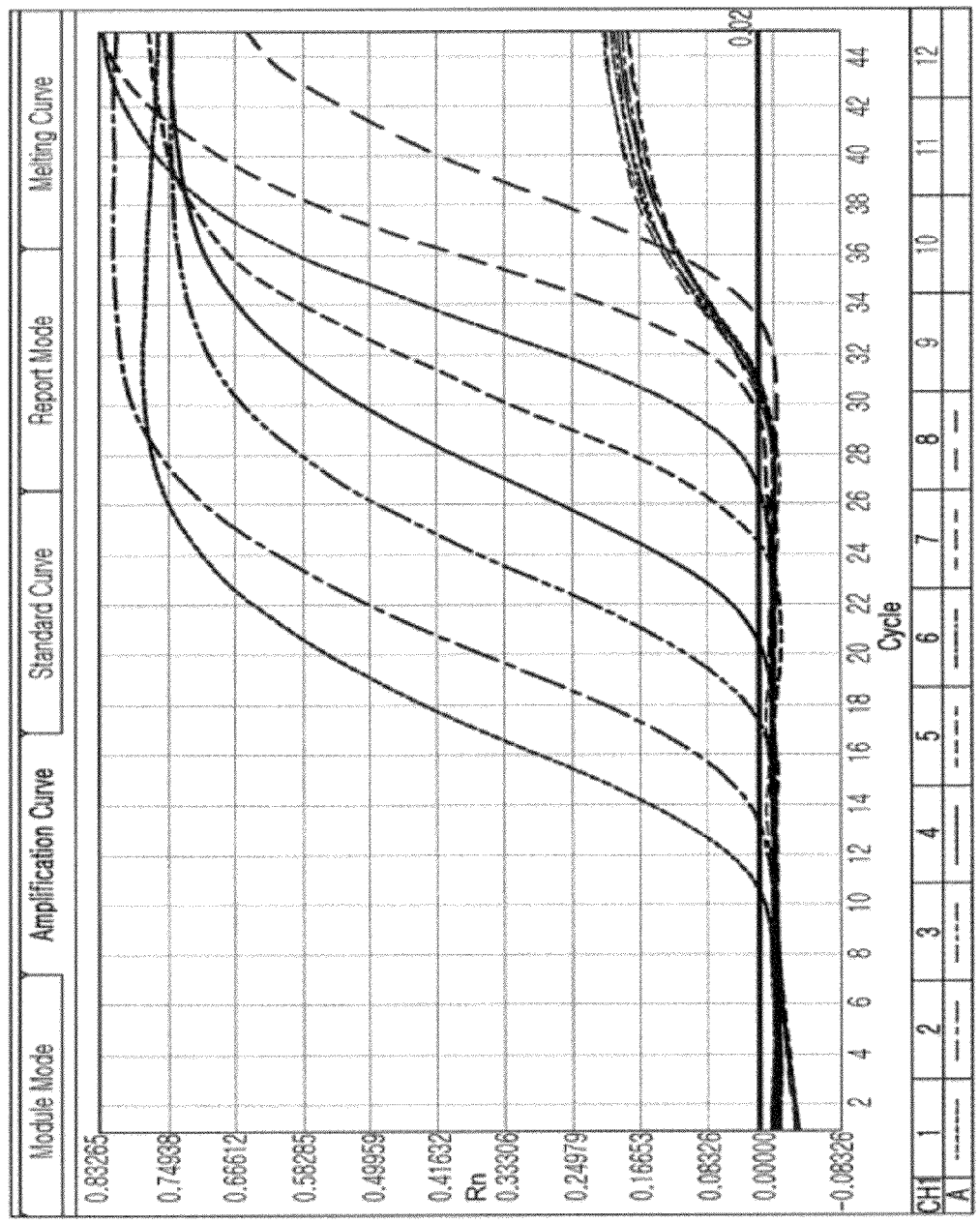

FIG. 2 provides the results showing that a positive detection can be made without competitive inhibition of the internal control being specific to MS2 bacterio phage for the HCV-specific primer and probe.

DETAILED DESCRIPTION OF THE INVENTION

In accordance with one aspect, the present invention relates to a composition for detection of HCV by a single step reaction, comprising the primer sequences of SEQ ID NOs:1 and 2.

As used herein, the term 'primer' means a short nucleic acid sequence having the free 3'-OH group, which forms a base-pair with a complementary template and serves as a starting point for template strand replication. The primer is able to initiate DNA synthesis in the presence of four different nucleoside triphosphates and an agent for polymerization (i.e., DNA polymerase or reverse transcriptase) in an appropriate buffer and at a suitable temperature. The primer of the present invention can be chemically synthesized by the phosphoramidite solid support method or other well-known methods.

The primer of the present invention is a novel primer specific to HCV 5'-UTR. The present invention provides a composition for HCV detection, comprising a sense primer having the base sequence of SEQ ID NO:1 and/or an antisense primer having the base sequence of SEQ ID NO:2 and a probe having the base sequence of SEQ ID NOs:5 or 9. Preferably, the present invention provides excellent sensitivity and specificity in the detection of HCV in blood by using the 5'-UTR specific primer and probe. The base sequences of the primers are described in the following Table 1.

TABLE 1

Primer Base Sequence

| Name | Base sequence | Length | SEQ ID NO: |
|------|---------------|--------|------------|
| CVFOR | CCC CTG TGA GGA ACT WCT GTC TTC | 24 | 1 |
| CVREV | GCA GAC CAC TAT GGC TCT CC | 20 | 2 |
| ICFOR-1 | CGA TGG CCC TGT CCT TTT ACA TTT A | 25 | 3 |
| ICREV-1 | CTT TTC GTT GGG ATC TTT GAT TAA A | 25 | 4 |
| ICFOR-2 | CCT CCG TTC GCG TTT ACG | 18 | 7 |
| ICREV-2 | TTG GCC CCA GTC GAG TTA A | 19 | 8 |

In Table 1, CVFOR is a novel forward primer being specific to HCV 5'-UTR, and its base sequence is described in SEQ ID NO:1, and CVREV is a novel reverse primer being specific to HCV 5'-UTR, and its base sequence is described in SEQ ID NO:2. ICFOR-1 is an internal control forward primer being specific to GFP, and its base sequence is described in SEQ ID NO:3, and ICREV-1 is an internal control reverse primer being specific to GFP, and its base sequence is described in SEQ ID NO:4. ICFOR-2 is an internal control forward primer being specific to MS2 bacteriophage, and its base sequence is described in SEQ ID NO:7. ICREV-2 is an internal control reverse primer being specific to MS2 bacteriophage, and its base sequence is described in SEQ ID NO:8.

As used herein, the term 'HCV (Hepatitis C virus)' is a virus, and causes hepatitis C that is commonly transmitted by blood transfusion. It was first discovered in 1989, and largely divided into acute and chronic hepatitis. The symptoms of acute hepatitis C are similar to those of hepatitis A and B. Most people have no symptoms, or some people experience flu-like symptoms, but recover without any treatment. The symptoms of chronic hepatitis C are also similar to those of hepatitis B, and include fatigue, fever, vomiting, muscle and joint pain. The symptoms continue for long periods of time, increasing the risk of development of hepatic cirrhosis and hepatoma. Therefore, continuous examination is required. PCR is generally used for diagnosis of hepatitis C, but has the disadvantages of separately performing amplification and detection steps after sample preparation. In the present invention, the 5'-UTR specific primer and probe are used to perform the amplification and detection steps in one reaction tube as a single reaction, whereby the convenience is improved, and the sensitivity and specificity are also increased.

In the preferred embodiment, the present invention can further include a probe sequence for detection of nucleic acid amplified by the primer sequences.

As used herein, the term 'probe' refers to an oligonucleotide (i.e., a sequence of nucleotides), whether occurring naturally or produced synthetically, recombinantly or by PCR amplification, which is capable of hybridizing at the least part of another oligonucleotide of interest. A probe can be single-stranded or double-stranded. Probes are useful in the detection, identification and isolation of particular gene sequences. In the preferred embodiment, it is contemplated that any probe used in the present invention will be labeled with any "reporter molecule," so that it is detectable in any detection system including fluorescent, radioactive, and luminescent systems. It is not intended that the present invention be limited to any particular detection system or label. Preferably, the probe of the present invention is a probe represented by SEQ ID NOs:5 or 9, and in the preferred Example of the present invention, it was found that the primer and probe were used to detect the presence of HCV, thereby obtaining the result with high sensitivity and specificity.

In one preferred embodiment, the probe of the present invention can be a probe having fluorescent molecules at its 5' and 3' ends. In one preferred embodiment, the probe contains a fluorescent reporter and a quencher at its 5' and 3' ends, respectively, in which they can show interference with each other. Therefore, when the probes bind to 5'-UTR in the sample, the generation of fluorescent signals is restricted. Upon performing polymerase chain reaction, the probe is decomposed, and the fluorescent reporter at the 5' end is released away from the quencher at the 3' end, thereby generating fluorescent signals. The presence of HCV in the sample can be detected by the fluorescent signals.

Any fluorescent molecules that are typically used in the related art can be labeled at the 5' end without limitation, and are exemplified by 6-carboxyfluorescein (FAM), hexachloro-6-carboxyfluorescein (HEX), tetrachloro-6-carboxyfluorescein, Cyanine-5 (Cy5), but are not limited thereto.

Any fluorescent molecules that are typically used in the related art can be also labeled at the 3' end without limitation, and are exemplified by 6-carboxytetramethyl-rhodamine (TAMRA) and BHQ-1, 2, 3 (black hole quencher-1, 2, 3), but are not limited thereto.

In the present invention, base sequences of the probes of SEQ ID NOs:5, 6, and 9 are described in the following Table 2.

TABLE 2

Probe Base Sequence

| Name | Base sequence (5'→3') | Length | SEQ ID NO: |
|---|---|---|---|
| CVFAM-1 | FAM CTA GCC ATG GCG TTA GTA YGA GTG TCG TAMRA | 27 | 5 |
| CVFAM-2 | FAM CTA GCC ATG GCG TTA GTA YGA GTG TYG TAMRA | 27 | 9 |
| ICCy5 | Cy5 ATT ACC TGT CCA CAC AAT CTG CCC TT BHQ3 | 26 | 6 |

In Table 2, CVFAM-1 and CVFAM-2 are probes targeting the 5'-UTR region of HCV virus and their base sequences are described in SEQ ID NOs:5 and 9, respectively. Their 5'-ends are labeled with FAM, and their 3'-ends are labeled with TAMRA. In addition, ICCy5 is a probe targeting GFP, and its base sequence is described in SEQ ID NO:6. Its 5'-end is labeled with Cy5, and its 3'-end is labeled with BHQ3.

In the present invention, the primers of SEQ ID NOs:1 and 2 and the probes of SEQ ID NOs:5 and 9 target the 5'-UTR region of HCV. The 5'-UTR region is a highly conserved region of about 340 bp, and has a stem-loop structure, and contains IRES (internal ribosomal entry site). See Tsukiyama-Kohara et al., *J. Virol.* 66:1476-83 (1992).

The HCV-specific primer and probe are able to produce the PCR product having a length of 100 bp, which is suitable for Real Time PCR. In particular, the 5'-UTR specific probe is useful for PCR quantification analysis by taqman assay or molecular beacon assay.

The present inventors have examined the risk of false positive and false negative results by base sequence analysis. They found that the primer of the present invention is a primer base sequence capable of amplifying the HCV gene only, and the primer and probe of the present invention shows a 100% positive predictive value in the test using the Genotype Panel (code 02/202) provided by NIBSC, indicating very low risk of false positive and false negative results. Accordingly, the primers of SEQ ID NOs:1 and 2 and the probes of SEQ ID NOs:5 and 9 are used to perform the detection of HCV with high reliability.

In the preferred embodiment, the present invention can include additional primer and probe sequences as an internal control to minimize the false positive and false negative results. The internal control group serves as a marker for direct comparison to prevent false positive and false negative results.

Preferably, the internal control group can be a GFP (Green Fluorescence Protein) derived from a plant or RNA virus, especially MS2 bacteriophage. More preferably, the GFP primer sequence can include the primers represented by SEQ ID NOs:3 and 4 (see Table 1). And more preferably, the MS2 primer sequence can include the primers represented by SEQ ID NOs:7 and 8 (see Table 1).

The primer and probe as the internal control group for prevention of false negative results are a primer and probe that are specific to the GFP (Green Fluorescence Protein) gene derived from a plant or MS2 bacteriophage, and do not inhibit the Real Time PCR of the HCV-specific primer and probe, and separately form PCR products. Particularly, in the detection of a low level of HCV, the formation of HCV PCR product is not inhibited by the PCR product of the internal control, whereby false negative results can be effectively prevented. Moreover, when RNA virus is used as an internal control, the entire virus particle, not naked RNA or DNA, is used as an internal control. Thus, the stability of the material used can be ensured, and RNA extraction, Reverse Transcription and PCR processes can be also performed more exactly. The probe base sequences for internal control are shown in Table 2.

In the preferred embodiment, the present invention can include additional enzymes for PCR in order to detect the presence of HCV in one reaction tube. Preferably, the enzymes can be MMLV and HS-Taq.

MMLV, which is a reverse transcriptase, is a RNA-dependent DNA polymerase encoded by MMLV (Moloney Murine Leukemia Virus) reverse transcriptase. The MMLV reverse transcriptase synthesizes the complementary DNA from a single-stranded RNA template to which a primer has been hybridized. The MMLV of the present invention synthesizes DNA from the HCV RNA template, allowing the subsequent PCR analysis. Thus, the presence of HCV in the sample can be detected.

HS-Taq is a modified form of Taq DNA polymerase, which is activated by heat treatment, and a chemical moiety is attached to the enzyme at the active site, which renders the enzyme inactive at room temperature. Thus, during the amplification process, misprimed primers are not extended. The result is higher specificity and greater yields when compared to standard DNA polymerases.

In the known RT-PCR using MMLV and HS-Taq, a part of the product that was formed by reverse transcription using MMLV was transferred to a new reaction tube, and then PCR was separately performed using HS-Taq. Therefore, the quantification results vary depending on the amount of the transcript from the primary reverse transcription, which can result in the inhibition of PCR. Accordingly, it is hard to detect HCV, and the procedures should be separately performed, which is inconvenient.

The present invention provides a composition for effectively detecting a specific gene in one reaction tube by a single step reaction, in which the accuracy of quantitative determination is improved by control of the compositions of MMLV and HS-Taq, and a buffer. When the composition of the present invention is used to perform the reverse transcription and PCR at the same time, it can greatly save labor and time, providing convenience, high specificity and sensitivity, and improved accuracy of quantitative determination.

The specific compositions of the primer, probe, MMLV, HS-Taq and buffer of the present invention are described in the following Table 3.

TABLE 3

| | Addition | Added amount (μl) |
|---|---|---|
| Primer | 100 μM CVFOR | 0.25 |
| | 100 μM CVREV | 0.25 |
| | 100 μM ICFOR | 0.25 |
| | 100 μM ICREV | 0.25 |
| Probe | 100 μM CVFAM | 0.15 |
| | 100 μM ICCy5 | 0.15 |
| PCR reactant | 5X MMLV Buffer | 10 |
| | 200U MMLV | 0.625 |
| | 2.5U HS-Taq | 1 |
| | 2 mM dUNTP | 3.5 |
| | 40U Rnasin | 0.2 |
| Extracted RNA | | 20 |
| Milli-Q Water | | 13.375 |
| Total | | 50 |

As described above, when two enzymes of MMLV and HS-Taq are used to perform the reverse transcription and PCR in one reaction tube at the same time, the detection of HCV can be qualitatively carried out by a single step reaction. The present invention provides amplification reaction in one reaction tube. The target amplification reaction can be preferably PCR. The PCR conditions are described in the following Table 4.

TABLE 4

| Reaction Conditions of Real Time PCR | |
|---|---|
| Temperature/Time | Cycle |
| 46° C./45 min or | 1 |
| 42° C./30 min | |
| 95° C./10 min | 1 |
| 95° C./15 sec | 45 |
| 62° C./60 sec | |
| 72° C./20 sec | |

In another preferred embodiment, the preset invention provides a composition for detecting HCV by a single step, further comprising a buffer, DNA polymerase, dNTP and sterile distilled water.

The buffer, DNA polymerase, dNTP and distilled water can be any solutions and enzymes that are typically used in the related art, without limitation. The composition according to Table 3 is preferred.

In still another embodiment, the present invention relates to a method for detecting HCV by a single step reaction, comprising the steps of obtaining a sample from a subject and amplifying HCV nucleic acid using the primer and detecting HCV nucleic acid using the probe.

The sample used in the present invention can be any sample that is expected to contain the HCV sequence, and preferably a sample that is obtained from the blood of patients with suspected HCV infection.

The amplification step of the present invention can be performed by any DNA amplification methods that are typically used in the related art, preferably PCR.

When the composition according to the present invention is used, reverse transcription of RNA extracted from clinical specimens, amplification of DNA, and real time PCR analysis can be performed in one reaction tube simultaneously.

Such real time PCR analysis can be performed by any commercially available Real-time PCR reactor, exemplified by SLAN real time PCR detection system (LG Life Science, Korea), LightCycler™ (Roche, Germany), ABI PRISM™ 7000/7700 (Applied Biosystems, USA), iCycler™ (Bio-Rad, USA), Rotor-Gene™ (Corbett, Australia), and Opticon™ (PharmaTech, USA), but is not limited thereto.

Preferably, the amplification and detection steps of the present invention can be performed in one reaction tube by a single step.

In the known methods, as described above, a part of the DNA product obtained from reverse transcription is transferred to a new reaction tube, and then PCR is separately performed. Therefore, the quantification results vary depending on the amount of the transcript from the primary reverse transcription, which can result in the inhibition of PCR. Accordingly, it is hard to detect HCV, and the procedures must be separately performed, which is inconvenient. However, the present invention provides a composition for effectively detecting a specific gene in one reaction tube by a single step reaction, in which the accuracy of quantitative determination is improved by control of the compositions of MMLV and HS-Taq, and the buffer. The compositions are described in Table 3.

In still another embodiment, the present invention relates to a kit for detection of HCV, comprising the primer and probe.

Preferably, the kit is manufactured by including the primer and probe having the sequences of the present invention, and the internal control primer and probe sequences. The kit can include a buffer, KCl, MgCl2, and dNTP for HCV detection. More preferably, the kit having the composition of Table 3 is manufactured to perform the amplification and detection of HCV in one reaction tube by a single step reaction. In the preferred Example of the present invention, a kit was manufactured according to the above composition, providing HCV detection with high sensitivity and specificity.

Hereinafter, the present invention will be described in more detail with reference to Examples. The Examples are provided only for the purpose of illustrating the present invention, and accordingly it is not intended that the present invention is limited thereto.

EXAMPLES

Example 1

Construction of Primer and Probe

It was confirmed that the HCV-specific primer and probe used in the present invention were primer sequences that can amplify only HCV virus by analyzing the DNA sequence, deposited with accession No. NC000962 in GenBank (ncbi.nlm.nih.gov) managed by the National Center for Biotechnology Information (NCBI) of the U.S. National Institutes of Health (NIH), using a DNAsis program from the company Hitachi Software, sequencing the DNA sequence, and then analyzing the DNA sequence again with BLAST (ncbi.nlm.nih.gov/BLAST/.

After obtaining the base sequence, the RNA virus- or plant-derived gene specific primer and probe that did not competitively inhibit the HCV-specific primer and probe in the composition for HCV detection were determined by performing reverse transcription and PCR at the same time in one reaction tube using MMLV and HS-Taq.

Example 2

Synthesis of Primer

The primers analyzed in Example 1 were synthesized by Metabion (Germany) using the method such as "Synthesis of Oligonucleotide" described in a paragraph 10.42 of Molecular cloning 3rd (Sambrook and Russell, Cold Spring Harbor Laboratory Press, New York, USA, 2001). The base sequences of the synthesized primers are shown in Table 1, and the base sequences of the synthesized probes are shown in Table 2.

Example 3

Extraction of HCV RNA from Clinical Specimen

Serum or EDTA-Plasma was separated from the blood of patients with suspected HCV infection, and extracted using a silica membrane-based spin column such as QIAamp MineElute Virus Spin Column (Qiagen).

Example 4

Multiplex Real-Time PCR Analysis Using the Primer and Probe (1) A PCR reaction composition was prepared according to the compositions in Table 3, and PCR was performed under the conditions of Table 4 in SLAN real time PCR detection system (LG Life Science, Korea).

(2) The reaction products were measured in real-time, and the results were analyzed using a SLAN 8.0 program after completing the reaction.

(3) Table 5 shows the positive results for the Genotype Panel (code 02/202) provided by NIBSC, and FIG. 1 shows that a positive detection can be made without competitive inhibition of the internal control (primers of SEQ ID NOs:3 and 4 and probe of SEQ ID NO:6) for the HCV-specific primers of SEQ ID NOs:1 and 2 and probe of SEQ ID NO:5. And FIG. 2 shows that a positive detection can be made without competitive inhibition of the internal control (primers of SEQ ID NOs:7 and 8 and probe of SEQ ID NO:6) for the HCV-specific primers of SEQ ID NOs:1 and 2 and probe of SEQ ID NO:9. Especially, when RNA virus is used as an internal control, the entire virus particle, not naked RNA or DNA, is used as an internal control (primers of SEQ ID NO:7). Thus, the stability of the material used can be ensured, and RNA extraction, Reverse Transcription and PCR processes can be also performed more exactly.

TABLE 5

HCV RNA Genotype Panel for NAT, NIBSC Code 02/202

| Panel member | HCV Genotype | Ct value by AdvanSure HCV |
|---|---|---|
| NIBSC-1 | 1 | 32.24 |
| NIBSC-2 | 2 | 33.00 |
| NIBSC-3 | 3 | 33.27 |
| NIBSC-4 | 4 | 32.52 |
| NIBSC-5 | 5 | 32.07 |
| NIBSC-6 | 6 | 33.81 |

TABLE 6

Test of Detection Limit

| IU/mL | # Tested | # Detected | % Detected |
|---|---|---|---|
| 100 | 24 | 24 | 100 |
| 50 | 24 | 24 | 100 |
| 25 | 24 | 23 | 96 |
| 12.5 | 24 | 23 | 96 |
| 6.25 | 24 | 6 | 25 |
| Probit 95% Hit rate | | 18.5 IU/mL | |

In the test of detection limit, AdvanSure HCV Real-Time PCR detected the HCV RNA of 12.5 IU/mL by 95%. The 95% detection limit was 16.7 IU/mL and the 50% detection limit was 7.9 IU/mL by probit analysis. Note: the Probit 95% Hit rate of Abbott is 23.8 IU/mL.

TABLE 7

Test on Diagnostic Sensitivity

| | | No. of Sample | Results |
|---|---|---|---|
| Diagnostic sensitivity | | 100 | 99 positive |
| Diagnostic specificity | | 50 | All negative |
| Analysis specificity | HAV Positive | 13 | All negative |
| | HBV Positive | 20 | All negative |
| | HIV-1 Positive | 10 | All negative |

Note: Of 100 with chronic hepatitis C positive specimens in Abbott HCV Real-Time PCR, 99 specimens were positive, indicating diagnostic sensitivity of 99%. Of 50 healthy specimens that showed low HCV level below 30 IU/mL in Abbott HCV Real-Time PCR, all specimens showed negative, indicating diagnostic specificity of 100%. All negative results were also observed in HAV-, HBV-, and HIV-1-positive specimens, showing excellent analysis specificity.

TABLE 8

Test on Precision

| | Day 1 | Day 2 | Day 3 | Day 4 | Day 5 | Day 6 | Day 7 | Day 8 | Day 9 | Day 10 | AVG | ST. DEV. | CV (%) |
|---|---|---|---|---|---|---|---|---|---|---|---|---|---|
| High | 24.00 | 24.01 | 24.00 | 24.08 | 24.01 | 24.13 | 24.38 | 23.70 | 24.04 | 24.87 | 24.25 | 0.65 | 2.67 |
| | 24.00 | 24.27 | 24.00 | 24.50 | 23.75 | 23.55 | 26.30 | 23.82 | 24.08 | 25.50 | | | |
| Middle | 28.81 | 28.39 | 28.58 | 28.32 | 28.67 | 28.80 | 28.68 | 28.73 | 29.08 | 29.13 | 28.84 | 0.28 | 0.97 |
| | 29.41 | 28.82 | 28.64 | 28.72 | 28.65 | 29.00 | 29.14 | 29.09 | 29.11 | 29.09 | | | |
| Low | 33.21 | 33.20 | 33.63 | 32.40 | 33.45 | 33.66 | 34.66 | 34.18 | 35.18 | 35.04 | 33.65 | 0.92 | 2.73 |
| | 33.45 | 32.42 | 33.51 | 32.26 | 33.00 | 32.50 | 34.27 | 35.17 | 34.34 | 33.54 | | | |
| HPC | 20.06 | 20.66 | 20.00 | 19.38 | 20.28 | 20.31 | 21.24 | 22.00 | 21.82 | 22.00 | 20.78 | 0.93 | 4.49 |
| LPC | 35.78 | 36.59 | 35.47 | 34.06 | 37.53 | 37.87 | 37.06 | 37.43 | 38.64 | 37.82 | 36.83 | 1.37 | 3.72 |
| NC | NT | NT | NT | NT | NT | NT | NT | NT | NT | NT | | | |

Example 5

Clinical Test of the Kit of the Present Invention on HCV

The kit of the present invention comprising the HCV-specific primers of SEQ ID NOs:1 and 2 and probe of SEQ ID NO:5 and Abbott HCV genotyping kit were used to compare their diagnostic effect on HCV infection. The results of the clinical test are shown in the following Tables 6 to 8.

Herein, the term 'sensitivity' means the test positivity in disease, namely the ability of a test to correctly assess disease at a particular decision threshold.

The term 'specificity' means the test negativity in health, namely, the ability of a test to correctly assess the absence of disease at a particular decision threshold.

The breadth and scope of the present invention should not be limited by any of the above-described exemplary embodiments, but should be defined only in accordance with the following claims and their equivalents.

It is to be appreciated that the Detailed Description section, and not the Summary and Abstract sections, is intended to be used to interpret the claims. The Summary and Abstract sections may set forth one or more but not all exemplary embodiments of the present invention as contemplated by the inventor(s), and thus, are not intended to limit the present invention and the appended claims in any way.

The foregoing description of the specific embodiments will so fully reveal the general nature of the invention that others can, by applying knowledge within the skill of the art, readily modify and/or adapt for various applications such specific embodiments, without undue experimentation, without departing from the general concept of the present invention. Therefore, such adaptations and modifications are intended to be within the meaning and range of equivalents of the disclosed embodiments, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance.

All documents, articles, publications, patents, and patent applications mentioned in this specification are herein incorporated by reference to the same extend as if each individual publication or patent application was specifically and individually indicated to be incorporated by reference.

What is claimed is:

1. A composition for detection of HCV (Hepatitis C virus) by a single step reaction, comprising two sets of a primer pair and a probe, wherein the one set of a primer pair and a probe is specific to HCV 5' UTR region and consists of primer sequences of SEQ ID NOs: 1 and 2, and a probe sequence of SEQ ID NO: 5; and the other set of a primer pair and a probe consists of primer sequences of SEQ ID NOs: 3 and 4, and a probe sequence of SEQ ID NO: 6.

2. The composition according to claim 1 further comprising MMLV and HS-Taq.

3. The composition according to claim 2, further comprising a buffer, DNA polymerase, dNTP, and sterile distilled water.

4. The composition according to claim 3, comprising 100 µM each of the primers of SEQ ID NOs:1, 2, 3 and 4; 100 µM each of the probes of SEQ ID NOs: 5 and 6; 5×MMLV buffer; 200U MMLV; 2.5U HS-Taq; 2 mM dUTP; and 40 U Rnasin.

5. The composition according to claim 1, wherein said probe of said one set and said probe of said other set contain fluorescent molecules at 5' and 3'-ends.

6. The composition according to claim 5, wherein the fluorescent molecule at the 5'-end is selected from the group consisting of 6-carboxyfluorescein, hexachloro-6-carboxyfluorescein, tetrachloro-6-carboxyfluorescein, FAM (5-carboxy fluorescein), HEX (2',4',5',7'-tetrachloro-6-carboxy-4,7-dichlorofluorescein), and Cy5 (cyanine-5), and the fluorescent molecule at the 3'-end is selected from the group consisting of 6-carboxytetramethyl-rhodamine, TAMRA (5-Carboxytetramethylrhodamine), and BHQ3 (black hole quencher 3).

7. A method for detecting HCV by a single step reaction, comprising obtaining a sample from a subject and amplifying and detecting HCV using the composition according to claim 1.

8. The method according to claim 7, wherein the sample is blood, and the amplification is performed by PCR.

9. A kit for detection of HCV, comprising the composition of claim 1.

10. The kit according to claim 9, wherein the kit comprises: 100 µM each of the primers of SEQ ID NOs: 1, 2, 3 and 4; 100 µM each of the probes of SEQ ID NOs: 5 and 6; 5×MMLV buffer; 200U MMLV; 2.5U HS-Taq; 2 mM dUTP; and 40U Rnasin.

* * * * *

SEQUENCE LISTING

```
<160> NUMBER OF SEQ ID NOS: 9

<210> SEQ ID NO 1
<211> LENGTH: 24
<212> TYPE: DNA
<213> ORGANISM: Artificial Sequence
<220> FEATURE:
<223> OTHER INFORMATION: forward primer for CV

<400> SEQUENCE: 1
cccctgtgag gaactwctgt cttc                                              24

<210> SEQ ID NO 2
<211> LENGTH: 20
<212> TYPE: DNA
<213> ORGANISM: Artificial Sequence
<220> FEATURE:
<223> OTHER INFORMATION: reverse primer for CV

<400> SEQUENCE: 2
gcagaccact atggctctcc                                                   20

<210> SEQ ID NO 3
<211> LENGTH: 25
<212> TYPE: DNA
<213> ORGANISM: Artificial Sequence
<220> FEATURE:
<223> OTHER INFORMATION: forward primer 1 for IC

<400> SEQUENCE: 3
cgatggccct gtccttttac attta                                             25

<210> SEQ ID NO 4
<211> LENGTH: 25
<212> TYPE: DNA
<213> ORGANISM: Artificial Sequence
<220> FEATURE:
<223> OTHER INFORMATION: reverse primer 1 for IC

<400> SEQUENCE: 4
cttttcgttg ggatctttga ttaaa                                             25

<210> SEQ ID NO 5
<211> LENGTH: 27
<212> TYPE: DNA
<213> ORGANISM: Artificial Sequence
<220> FEATURE:
<223> OTHER INFORMATION: probe 1 for CVFAM

<400> SEQUENCE: 5
ctagccatgg cgttagtayg agtgtcg                                           27
```

```
<210> SEQ ID NO 6
<211> LENGTH: 26
<212> TYPE: DNA
<213> ORGANISM: Artificial Sequence
<220> FEATURE:
<223> OTHER INFORMATION: probe for ICCy5

<400> SEQUENCE: 6
attacctgtc cacacaatct gccctt                                         26

<210> SEQ ID NO 7
<211> LENGTH: 18
<212> TYPE: DNA
<213> ORGANISM: Artificial Sequence
<220> FEATURE:
<223> OTHER INFORMATION: forward primer 2 for IC

<400> SEQUENCE: 7
cctccgttcg cgtttacg                                                  18

<210> SEQ ID NO 8
<211> LENGTH: 19
<212> TYPE: DNA
<213> ORGANISM: Artificial Sequence
<220> FEATURE:
<223> OTHER INFORMATION: reverse primer 2 for IC

<400> SEQUENCE: 8
ttggccccag tcgagttaa                                                 19

<210> SEQ ID NO 9
<211> LENGTH: 27
<212> TYPE: DNA
<213> ORGANISM: Artificial Sequence
<220> FEATURE:
<223> OTHER INFORMATION: probe 2 for CVFAM

<400> SEQUENCE: 9
ctagccatgg cgttagtayg agtgtyg                                        27
```